United States Patent [19]

Mulligan

[11] Patent Number: 5,156,842
[45] Date of Patent: Oct. 20, 1992

[54] LIQUID SUSPENSION FOR ORAL ADMINISTRATION

[75] Inventor: Seamus Mulligan, Athlone, Ireland

[73] Assignee: Elan Corporation, PLC, Athlone, Ireland

[21] Appl. No.: 769,160

[22] Filed: Sep. 27, 1991

Related U.S. Application Data

[63] Continuation of Ser. No. 649,225, Jan. 28, 1991, abandoned, which is a continuation of Ser. No. 208,401, Jun. 17, 1988, abandoned.

[30] Foreign Application Priority Data

Jun. 19, 1987 [IE] Ireland .................. 1645/87

[51] Int. Cl.$^5$ .............. A61K 35/78; A61K 35/00; A61K 9/48; A61F 9/02
[52] U.S. Cl. .................. 424/195.1; 424/116; 424/437; 424/451; 424/457; 424/522; 424/600; 514/29; 514/199; 514/557; 514/558
[58] Field of Search .............. 424/195.1, 451, 457, 424/439, 522, 600, 116; 514/558, 937, 943, 951, 964, 29, 199, 557

[56] References Cited

U.S. PATENT DOCUMENTS

| | | | |
|---|---|---|---|
| 3,996,355 | 12/1976 | Song-Ling et al. | 514/86 |
| 4,181,721 | 1/1980 | Speck et al. | 514/178 |
| 4,525,339 | 6/1985 | Behl et al. | 426/16 |
| 4,780,322 | 10/1988 | Martani et al. | 424/501 |

FOREIGN PATENT DOCUMENTS

| | | | |
|---|---|---|---|
| 567598 | 8/1960 | Belgium. | |
| 3309763 | 9/1984 | Fed. Rep. of Germany. | |
| 0193914 | 10/1985 | Japan | 514/937 |
| 1432784 | 4/1976 | United Kingdom. | |
| 2166651 | 5/1986 | United Kingdom. | |

*Primary Examiner*—John W. Rollins
*Attorney, Agent, or Firm*—Marla J. Church

[57] ABSTRACT

A non-aqueous pharmaceutical liquid suspension having improved bioavailability for oral administration comprises an active ingredient suspended in an edible, non-aqueous carrier vehicle such as an oil, wherein the active ingredient is in the form of controlled release particles containing the active ingredient and optionally an excipient in intimate admixture with at least one non-toxic polymer, the particles being coated with, distributed through or adsorbed onto said polymer, and the particles further having an average size in the range 0.1 to 150 microns and a predetermined release of active ingredient.

10 Claims, 5 Drawing Sheets

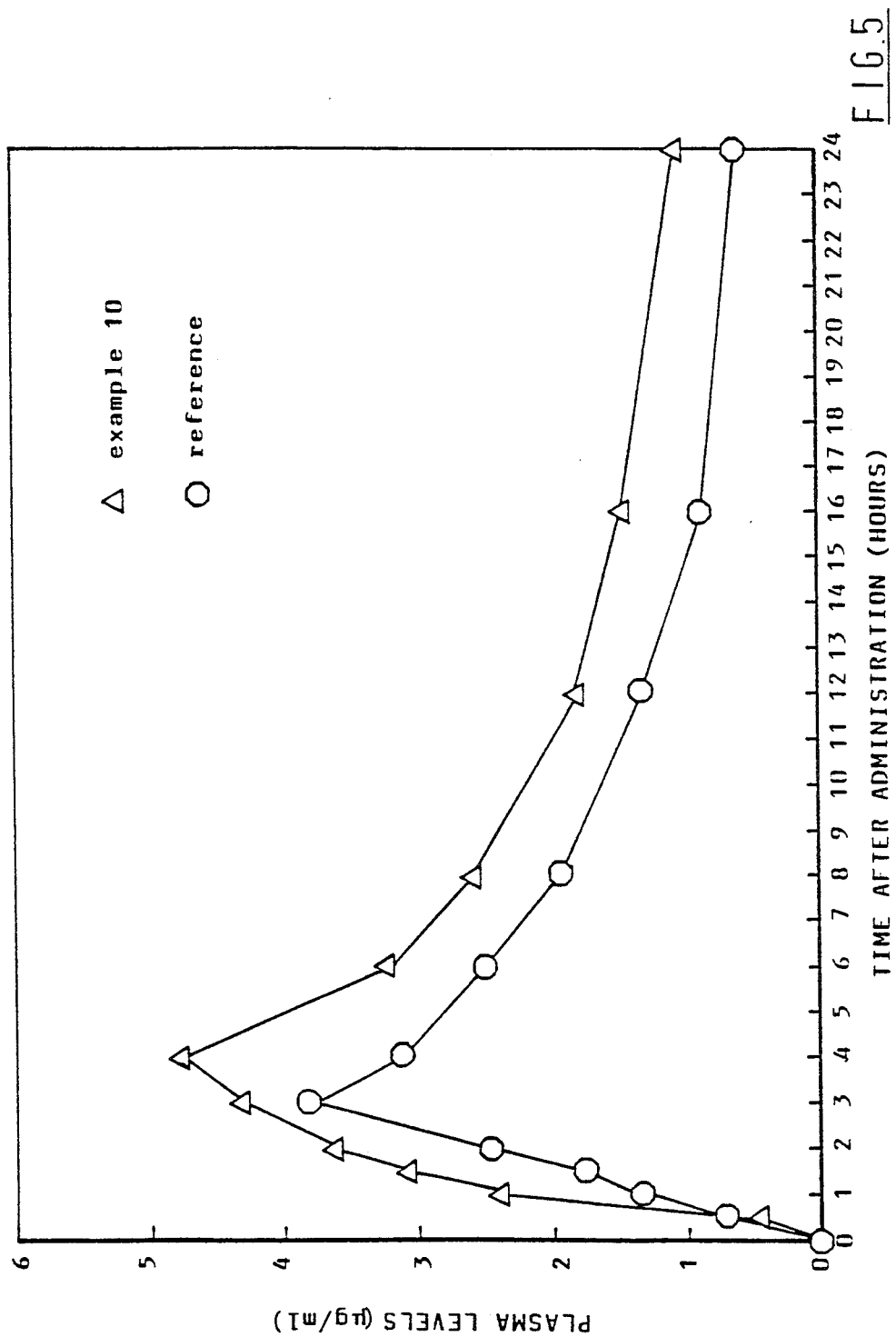

LIQUID SUSPENSION FOR ORAL ADMINISTRATION

This is a continuation of copending appending Ser. No. 07/649,225 filed on Jan. 28, 1991 abandoned, which is a continuation of Ser. No. 07/208,401 filed on Jun. 17, 1988 abandoned.

BACKGROUND OF THE INVENTION

This invention relates to liquid suspensions for oral administration. In particular, the invention relates to liquid suspensions with improved bioavailability, release characteristics, inter-subject variability, and taste characteristics when compared with conventional liquid formulations.

Liquid formulations conventionally used in human or veterinary medicine are generally aqueous based suspensions or, alternatively, emulsions. Conventional aqueous based suspensions are sold as reconstitutable suspensions or ready-made suspensions, the latter type of suspensions being common in the U.S.A. However, with both types of suspensions there are strict storage requirements such as a requirement for refrigeration. Storage problems with such formulations result from their having a short shelf life. For example, antibiotics frequently fall within this category, in that they are aqueous based products with a short shelf life necessitating stringent storage conditions.

SUMMARY OF THE INVENTION

Non-aqueous carrier vehicles have not conventionally been used in liquid formulations for oral administration. There has been limited use of oils in such formulations but these have been as oil-in-water emulsions or water-in-oil emulsions.

It is an object of the present invention to provide a non-aqueous based, liquid suspension for oral administration having good shelf life and, in addition, having improved bioavailability, release characteristics, inter-subject variability and taste characteristics relative to conventional liquid formulations.

Accordingly, the invention provides a liquid suspension for oral administration comprising an active ingredient suspended in an edible, non-aqueous carrier vehicle wherein the active ingredient is in the form of controlled release particles containing the active ingredient and optionally an excipient in intimate admixture with at least one non-toxic polymer, said particles being coated with, distributed through or adsorbed onto said polymer, and said particles further having an average size in the range 0.1 to 150 microns and a predetermined release of active ingredient.

Preferably the particles have an average size in the range 50 to 100 microns.

The non-aqueous carrier vehicle is preferably an oil of animal, mineral or vegetable origin. Preferably, the oil is of mineral or vegetable origin. Preferred oils of vegetable origin are selected from: almond oil, arachis oil, castor oil, fractionated coconut oil, cotton seed oil, ethyl oleate oil, evening primrose oil, maize oil, olive oil, persic oil, poppy-seed oil, safflower oil, sesame oil, soya oil and sunflower oil. Especially preferred vegetable oils include fractionated coconut oil, soya oil or sunflower oil. In the case of fractionated coconut oil, the oil is suitably that sold under the Trade Mark MIGYLOL (Dynamit Nobel). An especially suitable oil for use as the non-aqueous carrier vehicle is sucrose polyester as sold under the brand name Olestra.

In the case of mineral oils, suitable oils include silicone oil and paraffin or mineral oil.

Drug substances for use as active ingredient in the liquid suspension according to the invention include all major therapeutic classes, but especially antibiotics, more particularly macrolides such as Erythromycin and Roxithromycin, penicillins such as Amoxycillin trihydrate, antihistamines, antitussives, decongestants, expectorants, peptides, polypeptides and steroids. An especially suitable antitussive is dextromethorphan and an especially suitable expectorant is guaiphenesin. Especially suitable steroids are dehydroepiandrosterone and prednisolone. Dextromethorphan, guaiphenesin and potassium chloride are also particularly suitable for use as the active ingredient in the liquid suspension according to the invention.

It is found that the use of a non-aqueous vehicle as the carrier medium in suspension dosage forms according to the invention, either in capsule or liquid form, results in the performance of the active ingredient, in terms of its bioavailability, release characteristics, inter-subject variability, and taste characteristics being considerably improved over conventional liquid formulations.

In the case of antibiotics, the use of the non-aqueous carrier vehicle will normally allow the product to exist as a ready-made suspension with an acceptable shelf life at normal and elevated temperatures without refrigeration. This advantage is extremely important when dealing with products that may have to be reconstituted where the water supply and storage facilities are poor.

The improvement in bioavailability in presence of controlled release characteristics may allow a lowering in the total daily dose and also the number of dosing intervals. This will be expected to result in a reduced incidence of side effects due to decreased total dose, and improved patient compliance, due to the increase in dosage interval.

The performance, both physiological and organoleptic, of the suspension according to the invention can be altered as necessary depending on the specific drug entity. Therefore, inclusion of sweetening agents such as sorbitol may be required to enhance the palatability of the product. Similarly, flavourings, preservatives, colourings and other pharmaceutical excipients may be included to enhance the organoleptic properties of the suspension. The suspension may also include an antioxidant such as, for example, butylated hydroxyanisole, butylated hydroxytoluene or propyl gallate or a mixture thereof.

The addition of certain other excipients may serve to change the in vivo performance of the product, for example, the inclusion of pharmaceutically acceptable surfactants to modify the drug absorption rate.

The drug entity that included in the suspension has been treated so as to affect its taste or release properties, for example, by microencapsulation or by various processes which modify such properties. Alternatively, the drug entity may be in the form of an adsorbate, resinate or drug complex. A process whereby a taste-masked formulation of the raw material can be produced is a process in accordance with our UK-A-2 166 651. A material so produced and sold under the Trade Mark PharmaZome may have controlled release characteristics or may taste-mask the drug material. More specifically, products sold under the Trade Mark PharmaZome comprise a controlled release powder containing discrete microparticles for use in edible, pharmaceutical and other controlled release compositions, said powder comprising particles containing an active ingredient and optionally an excipient in intimate admixture with at least one non-toxic polymer, each of said particles being in the form of a micromatrix with the active ingredient and excipient, if present, uniformly distributed throughout, said particles further have an average size in the range 0.1 to 125 microns and have a predetermined release of active ingredient.

More generally, PharmaZomes are spherical drug/polymer mixtures with a particle size of less than 125 microns, this particle size being below the threshold of mouth feel. When incorporated into the non-aqueous vehicle carrier in the suspension according to the invention, they may reduce or eliminate the poor taste of some drug compounds.

BRIEF DESCRIPTION OF THE DRAWINGS

In the accompanying drawings:

FIG. 5 is a graph of plasma concentration ($\mu$g/ml) versus time after administration (hours) for the formulation of Example 10 relative to a reference product.

DETAILED DESCRIPTION OF THE INVENTION

Figure 1:
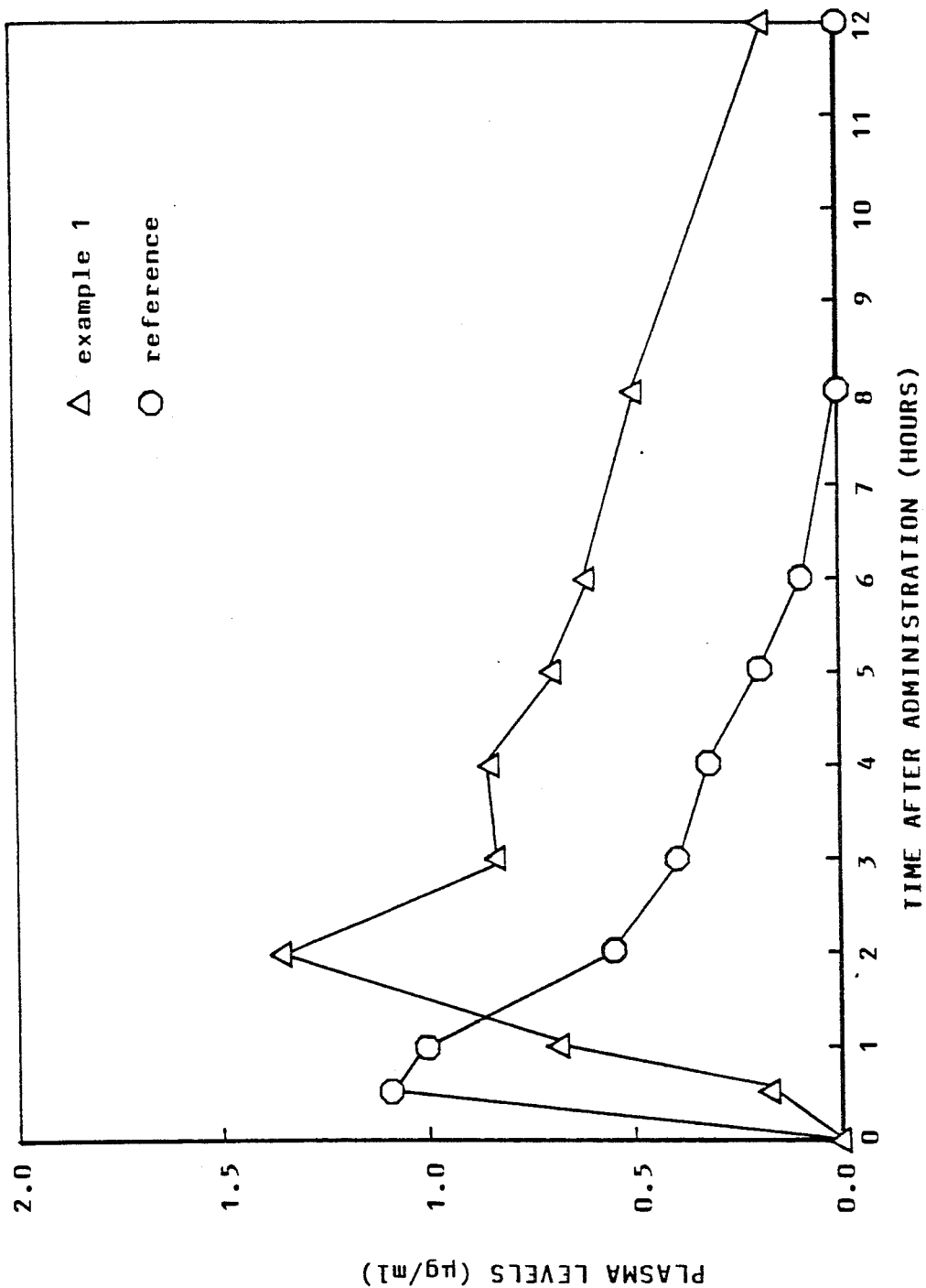
FIG. 1 is a graph of plasma concentration ($\mu$g/ml) versus time after administration (hours) for the formulation of Example 1 relative to a reference product.

The invention will be further illustrated by the following Examples.

EXAMPLE 1

Sorbitol (20 kg), citric acid (5 g) and Tenox GT-1 (20 g), were ball-milled with Soya Oil U.S.P. (76.7 kg) for twelve hours. The resulting dispersion of sorbitol in oil was transferred to a stirred vessel and the following added while stirring—Aerosil R972 (Aerosil is a Trade Mark) (3.1 kg), creamy vanilla flavour (100 g), candy mint flavour (75 g).

Erythromycin ethyl succinate PharmaZomes as prepared in accordance with UK-A-2 166 651 were added to the above liquid vehicle to produce a suspension containing the equivalent of 250 mg/5 ml of erythromycin as base. The formulation thereby produced was a ready-made suspension of Erythromycin ethyl succinate.

EXAMPLE 2

Aspartame (10 g), sucrose (0.5 kg) were milled through a number 200 mesh screen. The resulting powder was then added to silicone oil (9.225 kg). Also added while stirring was Bentone (0.25 kg), chocolate flavour (10 g) and vanilla flavour (5 g).

Potassium chloride PharmaZomes as produced in accordance with UK-A-2 166 651 were added to the vehicle to produce a suspension, containing 600 mg potassium chloride base/5 ml.

EXAMPLE 3

Example 1 was repeated except the oil used was sunflower oil.

EXAMPLE 4

Example 2 was repeated except the oil used was Migylol 812. Migylol is a Trade Mark of Dynamit Nobel and signifies grades of fractionated coconut oil.

EXAMPLE 5

Sucrose (1 kg) and Tenox GT-1 (1 g) were ball-milled with Soya Oil U.S.P. (8 kg). To the resulting dispersion was added the following —

| | |
|---|---|
| Aerosil (Trade Mark) | 0.4 kg |
| Butterscotch flavour | 0.01 kg |
| Vanilla flavour | 0.005 kg |
| Drewpol 3-1-0 | 0.2 kg |
| Drewpol 10-4-0 | 0.2 kg |

Drewpol is a Trade Mark of PVO International Inc. and is used to denote various grades of polyglyceryl partial esters of edible fats and/or oils or their fatty acids up to and including the decaglyceryl esters.

The mixture was well mixed to obtain an even dispersion. Amoxycillin trihydrate PharmaZomes as prepared in accordance with UK-A-2 166 651 were added to the above vehicle to obtain a suspension comprising 250 mg Amoxycillin as base per 5 ml.

EXAMPLE 6

Example 5 was repeated except taste-masked Amoxycillin coated with Ethocel in a fluid bed was included as the active ingredient to give a 250 mg Amoxycillin as base per 5 ml.

EXAMPLE 7

Example 1 was repeated except Erythromycin ethyl succinate coated with ethylcellulose was submitted in microcapsule form prepared by a coascervation method necessary adjustments were made to give a 250 mg Erythromycin as base per 5 ml suspension.

EXAMPLE 8

Example 5 was repeated, except the active material used was guaiphenesin PharmaZomes as prepared in accordance with UK-A-2 166 651 to produce a formulation containing 200 mg guaiphenesin per 5 ml.

EXAMPLE 9

Example 4 was repeated with Prednisolone PharmaZomes as prepared in accordance with UK-A-2 166 651 replacing Erythromycin ethyl succinate as the active ingredient to give a suspension potency of 1 mg/5 ml.

EXAMPLE 10

Roxithromycin (a macrolide) PharmZomes were prepared according to UK-A-2 166 651 with a potency of 712 mg/g. These Roxithromycin PharmaZomes were then incorporated into a pleasantly flavoured suspension vehicle to achieve a potency of 100 mg/5 ml, and provided for a pleasant tasting, ready-made suspension, exhibiting improved bioavailability, release and inter-subject variability. The final suspension consisted of:

| | |
|---|---|
| Cottonseed oil U.S.P. | 96.34% |
| Roxithromycin PharmaZomes | 2.81% |
| Tenox GT-1 (Trade Mark) | 0.05% |
| Aerosil R972 (Trade Mark) | 0.5% |
| Cherry flavour | 0.1% |
| Aspartame | 0.2% |

EXAMPLE 11

Potassium chloride microcapsules were manufactured using a coascervation process using cyclohexane as a solvent. Ethylcellulose (100 g) is dissolved in heated cyclohexane (1 kg) (about 75 degrees Celsius) and the potassium chloride (900 g) (milled to 75–100 microns) is suspended in the polymer solution. As the suspension is cooled, the ethylcellulose precipitates, coating the potassium chloride with the ethylcellulose. The microcapsules are under 150 microns in size and have a potency of 891 mg/g.

The potassium chloride microcapsules are then incorporated into a liquid suspension using a low calorific oil as the major vehicle component. The suspension consists of 600 mg (8 mEq) potassium chloride per 5 ml and is formulated as follows to give a pleasant tasting, ready-made suspension, which exhibits improved release and inter-subject variability.

| | |
|---|---|
| Potassium chloride microcapsules | 13.47% |
| Aspartame | 0.2% |
| Citric acid | 0.1% |
| Pharmasorb colloidal (Trade Mark) | 0.25% |
| Candy mint flavour | 0.05% |
| Vanilla flavour | 0.05% |
| Olestra oil (Brand name) (sucrose polyester) | 85.88% |

EXAMPLE 12

Dextromethorphan PharmaZomes were prepared according to UK-A-2 166 651 with a potency of 313 mg/g. The dextromethorphan PharmaZomes were incorporated into a pleasantly flavoured suspension vehicle to achieve a potency of 60 mg/5 ml. The suspension was formulated as follows:

| | |
|---|---|
| Sorbitol U.S.P. | 10.0% |
| Candy mint flavour | 0.1% |
| Aerosil R 972 (Trade Mark) | 0.2% |
| Tenox GT-1 (Trade Mark) | 0.05% |
| Dextromethorphan PharmaZomes | 3.83% |
| Migylol 812 (Trade Mark) | 85.82% |

Other drugs, polymers and solvents can be used in appropriate combinations to produce microcapsules of the type produced in Example 11.

PHARMACOLOGICAL DATA

1. The formulation of Example 1 was tested in six subjects in a two-way crossover single-dose comparison study with a reference product comprising a conventional reconstitutable suspension having an aqueous base of Erythromycin ethyl succinate and hereinafter referred to as "reference".

The reference was administered as 400 mg at 0 hours while the formulation of Example 1 was administered as 400 mg also at 0 hours. Plasma was sampled out to 12 hours and the mean results calculated and tabulated. The results are shown in Table 1 and accompanying FIG. 1. A range of pharmacokinetic parameters are given in Table 2 and time-cover in Table 3.

TABLE 1

Mean serum concentrations of Erythromycin (as ethyl succinate) comparing the formulation of Example 1 with reference.
No. of subjects: N = 6 (young healthy male subjects).
Plasma levels are in µg/ml.

| TIME (Hours) | REFERENCE | EXAMPLE 1 |
|---|---|---|
| 0.00 | 0.00 | 0.00 |
| 0.50 | 1.09 | 0.17 |
| 1.00 | 1.01 | 0.68 |
| 2.00 | 0.56 | 1.35 |
| 3.00 | 0.39 | 0.83 |
| 4.00 | 0.32 | 0.84 |
| 5.00 | 0.20 | 0.69 |
| 6.00 | 0.09 | 0.61 |
| 8.00 | 0.00 | 0.49 |
| 12.00 | 0.00 | 0.18 |

TABLE 2

Pharmacokinetic Parameters

| PHARMACOKINETIC PARAMETER | REFERENCE | EXAMPLE 1 |
|---|---|---|
| AUC (0–12 h) | 2.96 | 7.06 |
| AUC (0–∞) | 3.33 | 7.53 |
| F∞ (%) | 100.00 | 225.30 |
| Cmax | 1.22 | 1.51 |
| tmax | 0.58 | 2.67 |
| t ½ | 1.99 | 5.98 |
| Cmax/C(t) | 10.70 | 2.44 |

TABLE 3

Time-Cover (Hours)

| CONCENTRATIONS (µg/ml) | REFERENCE | EXAMPLE 1 |
|---|---|---|
| 0.25 | 4.15 | 9.11 |
| 0.50 | 2.17 | 5.57 |
| 0.75 | 1.04 | 3.07 |
| 1.00 | 0.48 | 1.59 |

DISCUSSION

From the above Tables and accompanying FIG. 1 it will be observed that the formulation of Example 1 shows remarkably increased bioavailability (F∞ = 225.30) compared to reference (= 100), as further witnessed by AUC (∞) values of 7.53 for the formulation of Example 1 compared to 3.33 for reference. This was further coupled with a clear demonstration of improved absorption as evidenced by the increased tmax (2.67 h) for the formulation of Example 1, compared to reference (= 0.58). The formulation also exhibits markedly extended time-cover at all concentration levels, but most noticeably for those up to 1.00 µg/ml, with the formulation of Example 1 giving 1.59 hours of cover at 1.00 µg/ml as against 0.48 hours for reference, over 3 times the time cover. The half-life (t ½) is also greatly increased for the formulation of Example 1 (5.98) compared to reference (1.99).

As both the formulation of Example 1 and reference have the same pharmaceutically active ingredient (Erythromycin ethyl succinate) and are administered in the same total dose over 12 hours, the following characteristics of:

* Greatly increased bioavailability
* Improved absorption

* Greatly increased time-cover at a range of plasma levels
* Markedly increased half-life result from the use of an oily vehicle as the carrier medium.

2. The formulation of Example 2 was tested in six subjects in an unblinded randomized, balanced cross over study with a reference product comprising K-lyte (K-lyte is a Trade Mark) 25 mEq effervescent tablets (hereinafter referred to as "reference").

In each case a single dose of 50 mEq was administered. In the case of reference this was administered in 6 fl. oz. water. In the case of the formulation of Example 2, each unit dose container was rinsed with water and the balance of remaining water was swallowed to a final volume of 4 fl. oz.

There were five days per treatment period with the two periods running consecutively. For each treatment period, the following was the regime for each of the 5 days.

| | Diet | Drug Administration |
|---|---|---|
| Day 1 | Fixed metabolic incl. 46 mEq K | None |
| Day 2 | " | None |
| Day 3 | " | None |
| Day 4 | " | 50 mEq KCl |
| Day 5 | " | None |

Six healthy male volunteers were enlisted and randomly allocated a subject number between 1 and 6. The dosage schedule was as follows:

| Subject number | Period 1 | Period 2 |
|---|---|---|
| 1, 3, 5 | Reference | Formulation of Example 2 |
| 2, 4, 6 | Formulation of Example 2 | Reference |

URINARY ELECTROLYTE LEVELS

Cumulative 24 hour urine samples were collected for Days 1, 2, 3 and 5. More frequent urine samples were collected on Day 4; 0-2, 2-4, 4-6, 6-8, 8-10, 10-12, 12-24 hours. In each case urinary volumes were noted. Subjects drank 100 ml per hour for 12 hours (8 am to 8 pm) daily and on initial study entry were given 500 ml of water to drink.

Urinary potassium was measured by atomic absorption spectrophotometry and results are expressed as urinary recovery (mEq). Results are summarised as mean ±s.d.

Calculations and Abbreviations

Urinary potassium (mEq) was calculated by multiplying the urinary concentration (mEq/ml) by the urinary volume (ml). Urinary volume is expressed simply in ml.

In addition the following parameters were calculated.

Au = Total recovery (mEq) for potassium and for volume.

Fu (%) = Relative bioavailability based on Au for Reference divided by Au for the formulation of Example 2.

Ru Max = Peak hourly recovery.

tu Max = Time of Ru max based on a mid-point sampling time for each sample.

Results

Figure 2:
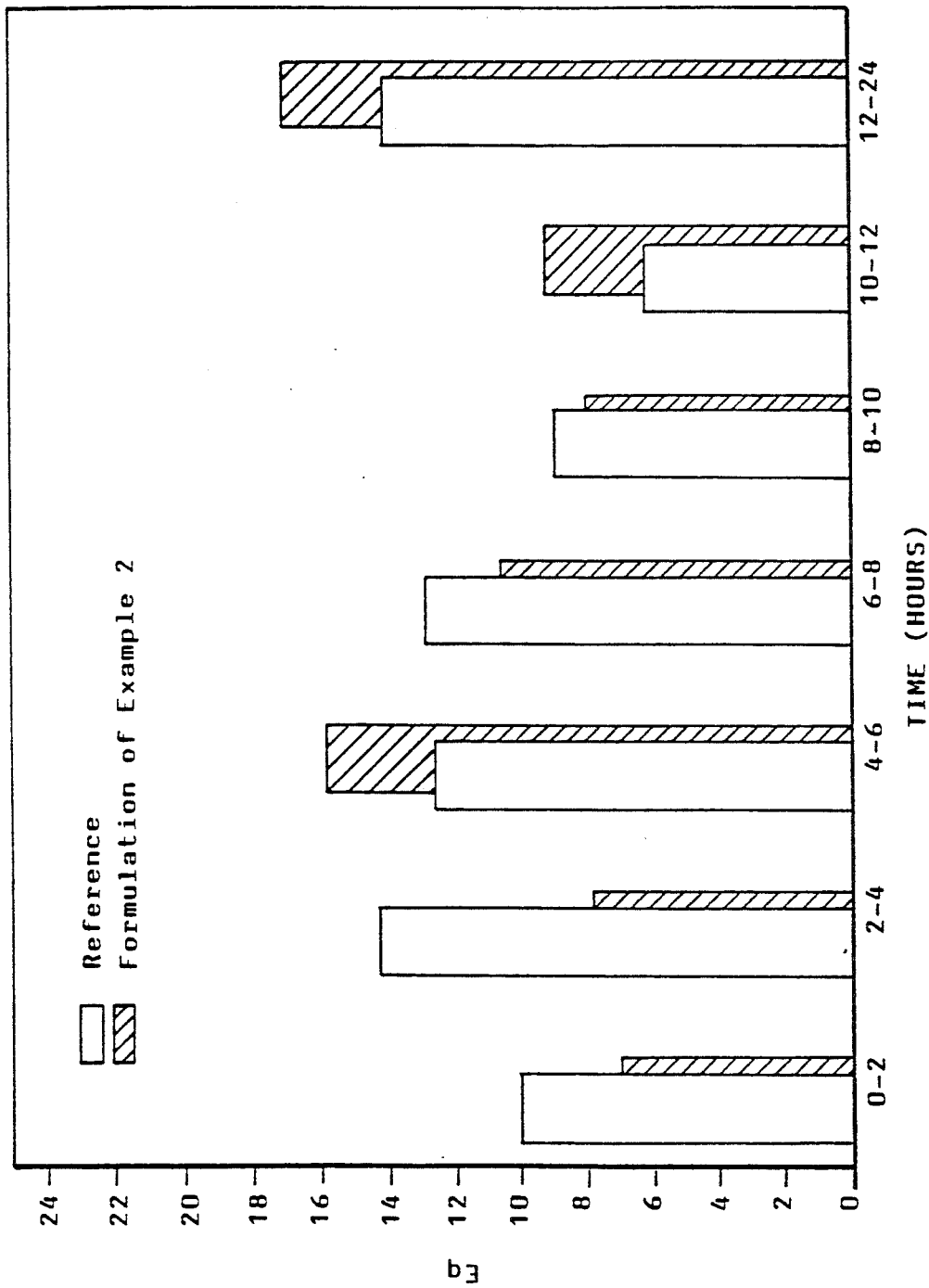
FIG. 2 is a histogram of potassium recovery (mEq) versus time (hours) for the formulation of Example 2 relative to a reference product.

The results are shown in Table 4 (potassium recovery) and accompanying FIG. 2 and in Table 5 (Urinary Parameters).

URINARY POTASSIUM RECOVERY

TABLE 4

| Cumulative 24-hour Recovery (mEq) (n = 6) | | | | |
|---|---|---|---|---|
| | Reference | | Formulation of Example 2 | |
| Day 1 | 52.32 | 22.07 | 65.63 | 18.88 |
| Day 2 | 49.68 | 17.19 | 48.15 | 18.86 |
| Day 3 | 52.92 | 17.02 | 58.93 | 16.86 |
| Day 4 | 78.94 | 11.82 | 75.36 | 15.87 |
| Day 5 | 55.50 | 19.95 | 58.77 | 22.42 |

TABLE 5

| Urinary Recovery Parameters: Potassium (n = 6) | | | | |
|---|---|---|---|---|
| | Reference | | Formulation of Example 2 | |
| Au | 78.94 | 11.82 | 75.36 | 15.87 |
| Fu (%) | 100 | | 95 | |
| Ru Max | 8.87 | 1.93 | 10.26 | 4.47 |
| tu Max | 5.67 | 1.63 | 5.00 | 3.35 |

DISCUSSION

The purpose of this study was to assess the bioavailabililty characteristics of the liquid KCl formulation prepared in Example 2 relative to the reference product.

It is clear from the results that both products are equivalent in terms of the addition of potassium excreted above the pre-determined stable baseline values. In fact the 24-hour urinary recovery of potassium following administration of the formulation of Example 2 was 95% that of the reference.

Detailed analyses of the pattern of urinary recovery over the course of Day 4 does suggest some differences in the rate of potassium absorption, although individuals within each group do differ in their pattern. Thus although the pattern of average recovery of potassium suggests a slightly slower rate of absorption with the formulation of Example 2, the time of peak hourly urinary recovery is actually earlier for the formulation of Example 2 than the reference product.

In conclusion, the results outlined above do indicate a similar extent of absorption for the formulation of Example 2 compared with the reference liquid. In addition the rate of absorption for both products is roughly similar with the same time of peak urinary recovery and only differing in the average extent of recovery over the first 4 hours after administration. Vastly improved taste characteristics as compared with conventional KCl formulations were obtained. This pleasant tasting suspension also has the advantage of being ready-made.

3. The formulation of Example 5 was tested in six subjects in a two-way crossover single-dose comparison study with a reference product comprising a conventional reconstitutable suspension having an aqueous base of Amoxicillin and hereinafter referred to as "reference".

Figure 3:
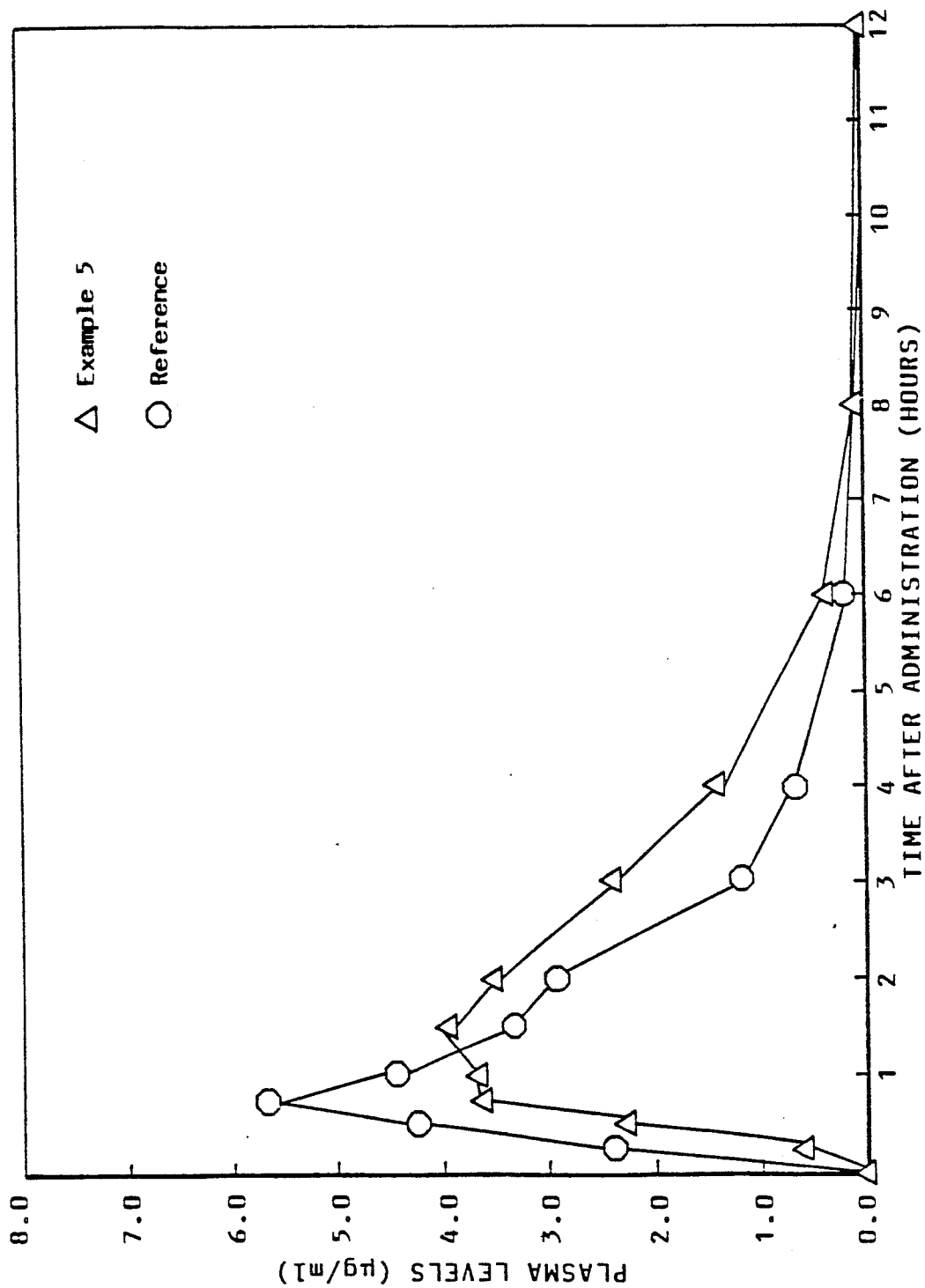
FIG. 3 is a graph of plasma concentration ($\mu$g/ml) versus time after administration (hours) for the formulation of Example 5 relative to a reference product.

Both the reference and formulation of Example 5 were administered as a single does of 250 mg at 0 hours. Plasma was sampled out to 12 hours and the mean results calculated and tabulated. The results are shown in Table 6 and accompanying FIG. 3. A range of pharmacokinetic parameters are given in Table 7.

TABLE 6

Mean serum concentrations of Amoxicillin comparing the formulation of Example 5 with reference.
No. of subjects: N = 6 (young healthy male subjects).
Plasma levels are in µg/ml.

| TIME (Hours) | REFERENCE | EXAMPLE 5 |
| --- | --- | --- |
| 0.00 | 0.00 | 0.00 |
| 0.25 | 2.41 | 0.58 |
| 0.50 | 4.25 | 2.29 |
| 0.75 | 5.69 | 3.63 |
| 1.00 | 4.44 | 3.67 |
| 1.50 | 3.37 | 3.95 |
| 2.00 | 2.91 | 3.52 |
| 3.00 | 1.18 | 2.40 |
| 4.00 | 0.66 | 1.40 |
| 6.00 | 0.18 | 0.36 |
| 8.00 | 0.06 | 0.07 |
| 12.00 | 0.00 | 0.00 |

TABLE 7

Pharmacokinetic Parameters

| PHARMACOKINETIC PARAMETER | REFERENCE | EXAMPLE 5 |
| --- | --- | --- |
| AUC (0–12 h) | 11.34 | 13.03 |
| AUC (0–∞) | 11.32 | 13.00 |
| F∞ (%) | 100.0 | 115.51 |
| tmax | 0.71 | 1.25 |
| Cmax | 5.99 | 4.80 |

DISCUSSION

The formulation of Example 5 exhibits increased bioavailability (F∞ = 115.51) compared to reference (= 100). A significant extension of the tmax is also observed, with 0.71 hours and 1.25 hours for reference and formulation of Example 5 respectively, thus exhibiting the improved absorption tendencies of the formulation in the oily vehicle. As both the reference and formulation of Example 5 contain the same pharmaceutically active ingredient and are administered at the same dose, it is apparent that the characteristics of:
* Increased bioavailability
* Improved absorption result from the use of an oily vehicle as the suspension medium for the formulation of Example 5.

4. The formulation of Example 6 was tested in five subjects in a two-way crossover single dose comparison study with a reference product comprising a conventional reconstitutable suspension having an aqueous base of Amoxicillin and hereinafter referred to as "reference".

Figure 4:
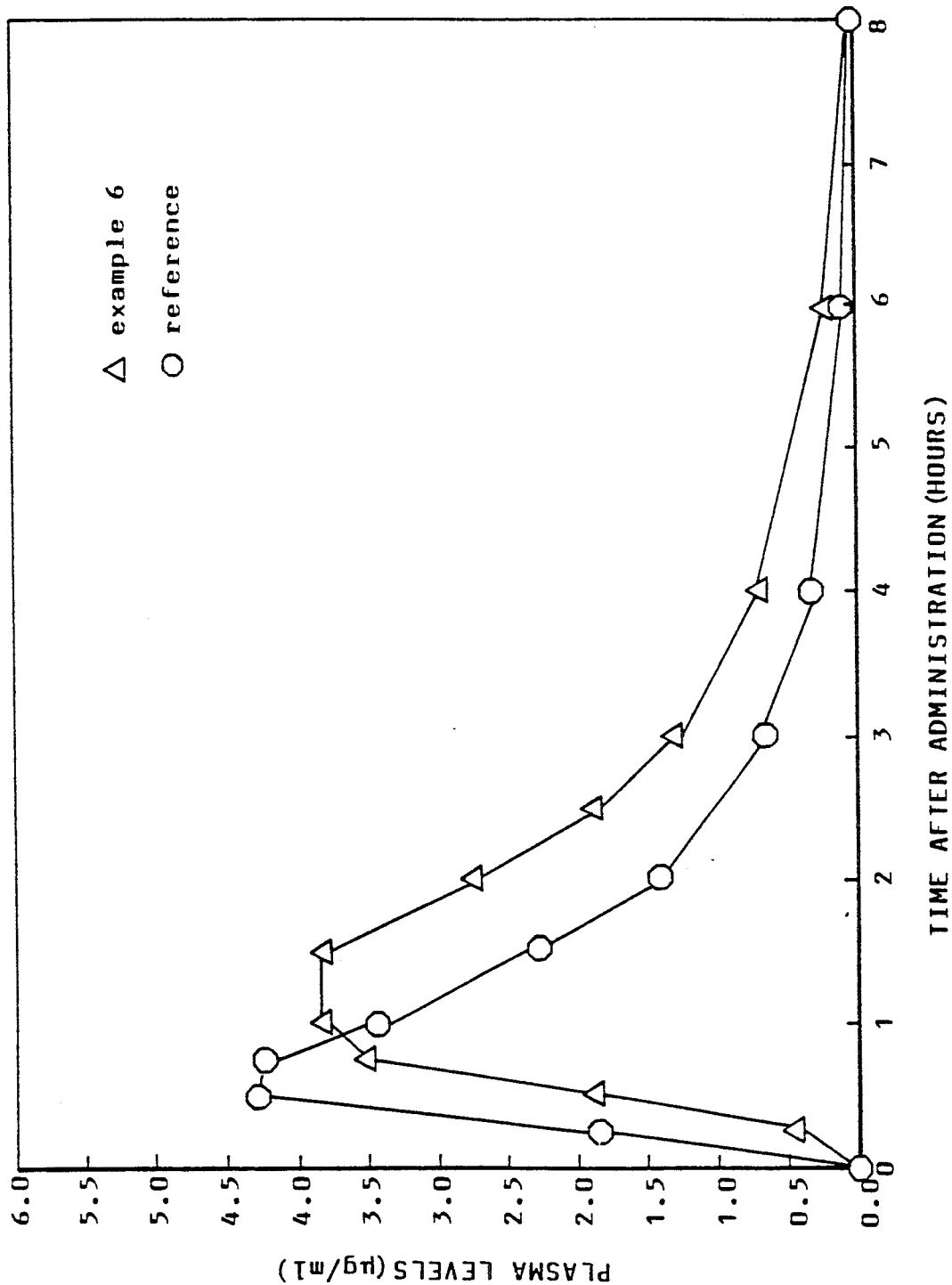
FIG. 4 is a graph of plasma concentration ($\mu$g/ml) versus time after administration (hours) for the formulation of Example 6 relative to a reference product.

Both the formulation of Example 6 and the reference were administered as a 125 mg does of Amoxicillin at 0 hours. Plasma was sampled out to 8 hours and the mean results calculated and tabulated. The results are shown in Table 8 and accompanying FIG. 4. A range of pharmacokinetic parameters are given in Table 9 and time-cover in Table 10.

TABLE 8

Mean serum concentrations of Amoxicillin comparing the formulation of Example 6 with reference.
No. of subjects: N = 5 (young healthy male subjects).
Plasma levels are in µg/ml.

| TIME (hours) | REFERENCE | EXAMPLE 6 |
| --- | --- | --- |
| 0.00 | 0.00 | 0.00 |
| 0.25 | 1.84 | 0.46 |
| 0.50 | 4.28 | 1.88 |
| 0.75 | 4.22 | 3.51 |
| 1.00 | 3.44 | 3.82 |
| 1.50 | 2.28 | 3.81 |
| 2.00 | 1.41 | 2.72 |
| 2.50 | — | 1.88 |
| 3.00 | 0.65 | 1.29 |
| 4.00 | 0.31 | 0.69 |
| 6.00 | 0.10 | 0.18 |
| 8.00 | 0.04 | 0.03 |

TABLE 9

Pharmacokinetic Parameters

| PHARMACOKINETIC PARAMETER | REFERENCE | EXAMPLE 6 |
| --- | --- | --- |
| AUC (0–8 h) | 7.42 | 9.50 |
| F (t) % | 100.00 | 128.03 |
| AUC (0–∞) | 7.50 | 9.58 |
| F∞ (t) % | 100.00 | 127.19 |
| Cmax | 4.61 | 4.29 |
| tmax | 0.60 | 1.10 |

TABLE 10

Time-Cover (Hours)

| CONCENTRATIONS (µg/ml) | REFERENCE | EXAMPLE 6 |
| --- | --- | --- |
| 1.00 | 2.42 | 3.09 |
| 2.00 | 1.38 | 1.90 |
| 3.00 | 0.79 | 1.05 |
| 4.00 | 0.29 | 0.37 |

DISCUSSION

The formulation as prepared in Example 6, exhibits an all round improvement in relation to in vivo performance. When compared with the reference, in a panel of five young healthy male subjects, a significant increase in overall bioavailability is acheived (F∞ = 127.19) over reference (= 100). This increased bioavailability is not, however, achieved to the detriment of the complete profile of the formulation of Example 6, but rather compliments the improved absorption characteristics obtained as witnessed by the tmax extension from 0.6 h with reference to 1.10 h with formulation of Example 6. A characteristic flattening of the overall curve is observed, with a concomitant depression in the Cmax. This profile points to the further advantages of reduced peak: trough ratio (Cmax/Cmin) which would be even more evident at steady-state. The slight depression in Cmax obtained with the formulation of Example 6, and the plateau-like curve-peak observed as a result, serve to increase the length of time over which various plasma levels of Amoxicillin are obtained, as evidenced by Time-cover, whereby increases are seen with the formulation of Example 6, in the amount of time in which plasma levels of 1.00, 2.00, 3.00 and 4.00 µg/ml are obtained.

Therefore, the formulation of Example 6 exhibits:
* Increased bioavailability over reference.
* Improved absorption characteristics.
* Decreased peak-to-trough fluctuations.

As the active ingredient is identical in chemical form and dose for both reference and the formulation of Example 6 it is obvious that the oily carrier vehicle is central in producing the observed improvements in performance. The formulation of Example 6 was also a pleasant tasting ready-made suspension.

5. The formulation of Example 10 was tested in three subjects in a two-way crossover single-dose comparison study with a reference product comprising Roxithromycin PharmaZomes in aqueous medium (i.e., an aqueous suspension) as a reconstitutable suspension and hereinafter referred to as "reference".

The reference was administered as 150 mg at 0 hours while the formulation of Example 10 was administered as 150 mg also at 0 hours. Plasma was sampled out to 24 hours and the mean results calculated and tabulated. The results are shown in Table 11 and accompanying FIG. 5. A range of pharmacokinetic parameters are given in Table 12 and time-cover in Table 13.

TABLE 11

Mean serum concentrations of Roxithromycin comparing the formulation of Example 10 with reference.
No. of subjects: N = 3 (young healthy male subjects).
Plasma levels are in μg/ml.

| TIME (Hours) | REFERENCE | EXAMPLE 10 |
| --- | --- | --- |
| 0.00 | 0.00 | 0.00 |
| 0.50 | 0.68 | 0.46 |
| 1.00 | 1.34 | 2.39 |
| 1.50 | 1.76 | 3.09 |
| 2.00 | 2.45 | 3.63 |
| 3.00 | 3.79 | 4.33 |
| 4.00 | 3.12 | 4.77 |
| 6.00 | 2.49 | 3.22 |
| 8.00 | 1.95 | 2.56 |
| 12.00 | 1.33 | 1.81 |
| 16.00 | 0.87 | 1.46 |
| 24.00 | 0.62 | 1.06 |

TABLE 12

| Pharmacokinetic Parameters | | |
| --- | --- | --- |
| PHARMACOKINETIC PARAMETER | REFERENCE | EXAMPLE 10 |
| AUC (0-24 h) | 36.06 | 51.54 |
| AUC (0-∞) | 43.86 | 75.66 |
| F∞ (%) | 100.00 | 195.17 |
| Cmax | 3.79 | 5.01 |
| tmax | 3.00 | 3.17 |
| $t_{\frac{1}{2}}$ | 8.88 | 16.21 |
| Cmax/C(t) | 6.12 | 4.66 |
| Kel | 0.08 | 0.043 |

TABLE 13

| | Time-Cover (Hours) | |
| --- | --- | --- |
| CONCENTRATIONS (μg/ml) | REFERENCE | EXAMPLE 10 |
| 1.00 | 15.03 | 20.51 |
| 2.00 | 5.75 | 9.88 |
| 3.00 | 1.89 | 5.05 |
| 4.00 | 1.13 | 1.93 |

DISCUSSION the above Tables and accompanying FIG. 5 it will be observed that the formulation of Example 10 shows remarkably increased bioavailability (F∞ = 195.17) compared to reference (=100), as further witnessed by AUC (∞) values of 75.66 for the formulation of Example 10 compared to 43.86 for reference. It is also clear from FIG. 5 that the formulation of Example 10 exhibits controlled absorption. Even after 24 hours post administration the formulation of Example 10 achieves plasma concentrations approximately twice those of reference. The formulation also exhibits markedly extended time-cover at all concentration levels. The half-life ($t_{\frac{1}{2}}$) is also greatly increased for the formulation of Example 10 (16.21) compared to reference (8.88).

As both the formulation of Example 10 and reference have the same pharmaceutically active ingredient (Roxithromycin) and are formulated similarly in accordance with UK-A-2 166 651 and are administered in the same total dose over 24 hours, the following characteristics of:

* Greatly increased bioavailability
* Improved absorption
* Greatly increased time-cover at a range of plasma levels
* Markedly increased half-life result from the use of an oily vehicle as the carrier medium. The formulation of Example 10 is also a pleasant tasting ready-made suspension.

What is claimed is:

1. A non-aqueous pharmaceutical liquid suspension having improved bioavailability for oral administration comprising an antibiotic suspended in an edible, non-aqueous carrier vehicle wherein the antibiotic is in the form of controlled release microparticles containing the antibiotic and optionally an excipient, the antibiotic of said microparticles being coated with, distributed through or adsorbed onto at least one non-toxic polymer, and said microparticles further having an average size in the range 0.1 to 150 microns and a controlled rate of release of antibiotic which in combination with the non-aqueous carrier vehicle permits controlled absorption of antibiotic effective to improve the bioavailability of said antibiotic over that obtained in aqueous liquid suspensions.

2. A liquid suspension according to claim 1, wherein the non-aqueous carrier vehicle is an oil selected from the group consisting of an animal oil, a mineral and an oil of vegetable origin.

3. A liquid suspension according to claim 2, wherein the oil is an oil of vegetable origin selected from the group consisting of almond oil, arachis oil, castor oil, fractionated coconut oil, cotton seed oil, ethyl oleate oil, evening primrose oil, maize oil, olive oil, persic oil, poppy-seed oil, safflower oil, sesame oil, soya oil, sunflower oil and sucrose polyester.

4. A liquid suspension according to claim 3, wherein the oil is selected from the group consisting of fractionated coconut oil, soya oil and sunflower oil.

5. A liquid suspension according to claim 2, wherein the oil is selected from the group consisting of paraffin oil and silicone oil.

6. A liquid suspension according to claim 1, wherein the antibiotic is selected from the group consisting of a macrolide or a salt thereof and a penicillin or salt or hydrate thereof.

7. A liquid suspension according to claim 6, wherein antibiotic is Erythromycin ethyl succinate.

8. A liquid suspension according to claim 6, wherein the antibiotic is Roxithromycin.

9. A liquid suspension according to claim 6, wherein the antibiotic is Amoxicillin trihydrate.

10. A liquid suspension according to claim 1, which is in the form of capsules.

* * * * *